(12) United States Patent
Kass et al.

(10) Patent No.: US 8,448,518 B2
(45) Date of Patent: May 28, 2013

(54) REMOVABLE WEAR-PLATE ASSEMBLY FOR ACOUSTIC PROBES

(75) Inventors: Daniel Stephen Kass, Attleboro, MA (US); Matthew Edward Stanton, Reading, MA (US); Thomas J. Nelligan, Waltham, MA (US)

(73) Assignee: Olympus NDT, Waltham, MA (US)

( * ) Notice: Subject to any disclaimer, the term of this patent is extended or adjusted under 35 U.S.C. 154(b) by 420 days.

(21) Appl. No.: 12/813,990

(22) Filed: Jun. 11, 2010

(65) Prior Publication Data

US 2011/0303013 A1     Dec. 15, 2011

(51) Int. Cl.
*G01N 29/28*     (2006.01)

(52) U.S. Cl.
USPC ............................................. 73/644

(58) Field of Classification Search
USPC .................. 73/431, 866.5, 432.1, 644
See application file for complete search history.

(56) References Cited

U.S. PATENT DOCUMENTS

| | | | | |
|---|---|---|---|---|
| 3,279,242 A * | 10/1966 | Megoloff | | 73/644 |
| 4,703,656 A * | 11/1987 | Bhardwaj | | 73/644 |
| 4,852,416 A * | 8/1989 | Boone et al. | | 73/866.5 |
| 5,741,971 A * | 4/1998 | Lacy | | 73/597 |
| 7,591,182 B2 * | 9/2009 | Sato et al. | | 73/649 |
| 7,637,163 B2 * | 12/2009 | Fetzer et al. | | 73/644 |
| 2006/0078131 A1 * | 4/2006 | Booth | | 381/71.1 |

* cited by examiner

*Primary Examiner* — Peter Macchiarolo
*Assistant Examiner* — Rose M Miller
(74) *Attorney, Agent, or Firm* — Ostrolenk Faber LLP

(57) ABSTRACT

Disclosed is a wear plate assembly for NDT/NDI probes which provides sufficient protection for the probe being wrung against test objects, desirable acoustic performance meeting the requirements for versatile ultrasonic inspections while providing a mechanism that allows the transducer to be put into or taken out conveniently. The wear plate protects probes from being pieced, worn or structurally deformed albeit being thinner than a wavelength of the acoustic echoes.

7 Claims, 4 Drawing Sheets

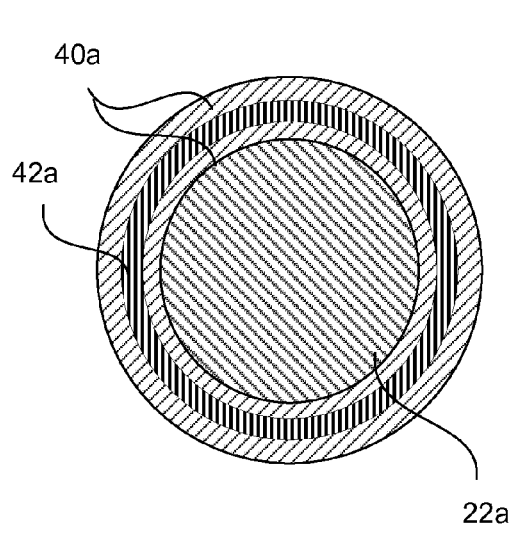
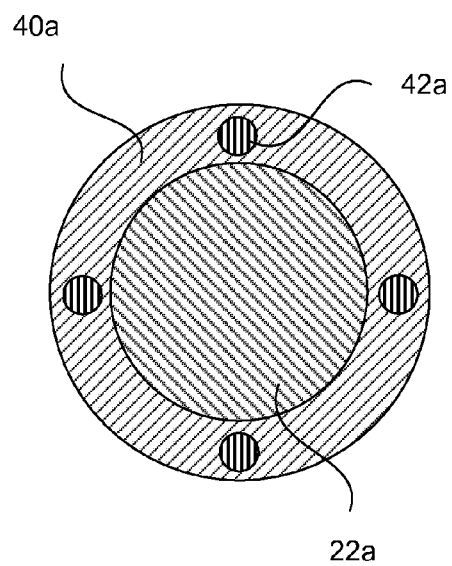
Fig. 3a    Fig. 3b
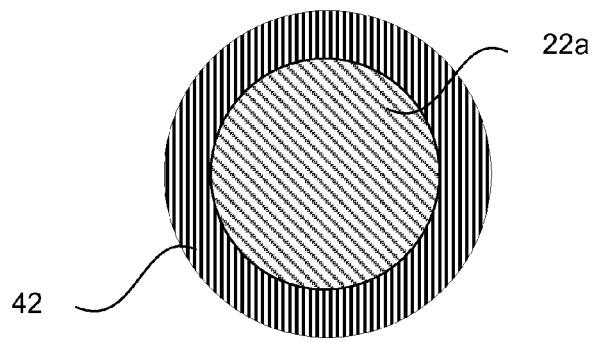
Fig. 3c

REMOVABLE WEAR-PLATE ASSEMBLY FOR ACOUSTIC PROBES

FIELD OF THE INVENTION

The present invention relates to an acoustic probe and probe accessory associated with non-destructive testing and inspection (NDT/NDI), more specifically to a removable covering assembly for preventing wear and damage to the probe that is used in contact with NDT/NDI test objects without introducing undesirable acoustic delay.

BACKGROUND OF THE INVENTION

Acoustic/ultrasonic probes used for contact inspections are wrung against and moved on test object surfaces. The wringing movement improves the signal by removing excess coupling liquid or gel from between the probe and the work surface. Probes are also moved on the surface to locate features or examine adjacent areas of the test object. The movement with force against rough, hard, and abrasive test object surfaces causes damage and premature wear of the probe contact surface. Severely worn or damaged probes require expensive repair or replacement and result in lost time.

The need for protective surfaces for ultrasonic probes and the fragile transducers within them is seen in the usage of many types of probes and probe accessories. Existing effort and means for protecting probes from damage and wear are known but present limitations of various kinds.

One kind of existing, integral protective surface is of plates of hard material such as tungsten carbide, titanium carbide cermets or aluminum oxide ceramics, which are often bonded across the face of probes to resist wear and damage. These hard wear plates plastically deform asperities on the test object surface and slide over them. However the hard wear plates must be thin relative to the ultrasonic wavelength in the material in order to maintain a good acoustic working range and broad inspection application. In addition, even hard plates eventually wear thin, particularly the perimeter of the hard plate and any portion of the probe housing near the perimeter are further subject to wearing forces greater than the central, planar surface of the plate. In addition, housing corners and brittle, thin, plate edges forcibly moved against surface protrusions may chip and break away, accelerating probe wear and damage. Bonded hard wear plates are not easily separated from other probe structures, making repair or replacement of damaged or worn parts difficult or not possible. The provided protection of hard plates is therefore limited by the wear of the plates, and the difficulty of repair or replacement.

It should be noted that wear plate is used herein to denote a thin, hard protective layer of, or attached to, a probe. The wear plate can be directly used between the transducer and the test object or between an integrally bonded protective surface of a probe and test object.

Another kind of integral, protective surface on probes is of plastic-like, acoustic impedance matching layers, which are bonded across the ultrasonic probe face to transfer acoustic energy into water, plastic or composite materials. These probes are not designed to be directly in contact with metal test objects as the relatively soft plastic face would wear out quickly when wrung against rough metal surfaces. The soft face does provide sufficient protection to the transducer for the probe to be fastened in static contact with removable accessory devices such as consumable plastic delay lines and wedges, rubber membranes or standoff assemblies which are coupled to the test object and limit probe wear. Probe efficiency is improved when the value of specific acoustic impedance of the layer, determined by the product of a materials density and ultrasonic velocity, lies between the specific acoustic impedance of the materials on either side of the layer. Plastic, water and composite materials have densities, velocities, and specific acoustic impedances that are much lower than hard materials such as carbides or ceramics. Therefore, probes designed to transmit sound into low acoustic impedance devices such as plastic delays and wedges are preferentially made with soft, plastic-like face layers. However, these integral, plastic-like, protective face layers do not provide sufficient protection to the probes. They need another measure of wear surface to be used in contact with test objects.

One kind of transducer used in highly efficient probes is a piezoelectric composite that incorporates piezoelectric ceramic in a polymer matrix to achieve desirable material characteristics. The lower acoustic impedance of the composite along with plastic-like, matching layers improves sound transmission into low impedance accessories such as plastic delay lines and wedges. The composites structure has the further advantage of reducing lateral coupling of sound energy, which makes the composites the preferred material for array probe designs including phased array probes. Particularly, array probes are generally designed with matching layers bonded to the piezoelectric composite for efficient sound transmission into plastic probe accessories. However, the plastic-like, soft-face layers are generally vulnerable to wear. In addition, array probes have high replacement cost. Therefore, array probes are not normally used for direct contact inspections and are often used with a plastic probe accessory. The use of plastic delay lines and refracting wedges, however, introduces an array of issues from increased operation complexity, to the impact of measurement accuracy and to noises introduced in the volume of the plastic accessories. Therefore, a wear plate is desirable that protects the soft faces of array and general piezoelectric composite probes, and does not adversely affect measurement of a test object.

Another type of existing protective surface is thin plastic plates or rubber like membranes, which are removable probe accessories, acoustically coupled with liquid or gel to the face of probes as protection from wear. Means such as threaded members are used to mechanically fasten the plates or membranes to the probes. When worn, the plastic plates, rubber membranes and fastening members are easily and economically replaced by the inspection operator. However, plastic and rubber like materials may not slide in a smoothly scanning motion because they plastically deform into the interstices of work surface asperities and increase friction. A further problem with thin plastic plates and flexible membranes is that they may be penetrated by relatively large and sharp, work surface protrusions and fail to adequately protect the probe. Thick layers would provide greater protection but degrade the range of inspection. In addition, in both cases of thin and thick plastic protective surfaces, delay-line multiple echoes presents problems for inspections.

Yet another kind of existing wear or protective measure is standoff assemblies, such as water boxes and carbide inserts used in a gap scanning technique. These removable accessories extend from the perimeter of probes towards work surfaces, providing a vacant volume between the probe and work surfaces. The probe and work surfaces are acoustically coupled through a liquid or gel flooding the volume between the surfaces. Liquid or gel that leaks from the volume requires frequent or continuous replenishment. Leaking fluid may need to be contained, cleaned up or re-circulated. Equipment for containment, re-circulation and replenishment may be costly and cumbersome or impractical to use at the inspection site. As with the thickness of hard plates, plastic plates, and rubber layers, the thickness of the liquid filled volume needs to be thin relative to a wavelength in the liquid to maintain a good working range. However, the standoff devices may not adequately protect probes from work surface protrusions that are larger than the standoff distance, which could often happen.

Another type of existing probe accessory serving as a wear surface is called ultrasonic delay lines, which are thick, solid blocks or enclosed liquid columns held between the probe and work surface. Sonic energy emitted from the probe, travels for a period of time within the delay line towards the work surface where it is partially reflected back from, and partially transmitted into the test object. Energy not initially reflected back from the work surface travels for a time within the test object until it is reflected by reflectors within the test object, back towards the delay line and probe. Further partial reflections and transmissions occur at the interfaces of the probe and delay line, and the delay line and work surface, causing repeated echo sequences known as delay line multiple echoes. The period of these reverberations is determined by sound speed and length of the delay line. Delay line multiple echoes that occur prior to or coincident with signal echoes from within the test object can interfere with signal interpretation and cause measurement inaccuracies. The practical inspection range is usually limited by the travel time within the delay line. Longer delays have longer delay times, but attenuation and sound beam spread increases with length. Attenuation reduces signal strength and causes frequency distortions of the signal. Beam spread reduces signal strength and causes additional noise echoes when the spreading beam reflects from the side of the delay line. Although thick delay lines and long water columns can provide good protection for probes, they limit the inspection range.

Thus given the existing types of wear protective measures for associated probes and their shortcomings of lack of sufficient protection, desirable acoustic performance and easiness of operation, an improved removable wear plate is needed to address the market voids.

Ultrasonic Testing of Materials by publisher Springer-Verlag, $4^{th}$ edition, section 10.4 gives a review of ultrasonic probes (transducers) and the associated wear or protective measures of various types. FIGS. 10.30, 10.32 and 10.34 are helpful to the understanding of the existing types of probes, wear plates or protective measures and their acoustic characteristics.

NDI devices, where existing wear protective measures either lack the sufficient protection for the probes from being wrung against test object, or the desirable acoustic performance, or operation efficiency.

Accordingly, it is a general object of the present disclosure to provide a wear plate assembly accessory for NDT/NDI probes, which provides sufficient protection for the probe being wrung against test objects, desirable acoustic performance meeting the requirements for versatile ultrasonic inspections while providing a mechanism that allows the wear plate to be put on and off conveniently.

It is further an object of the present disclosure to deploy a material for the wear plate assembly, that is substantially free of reverberation echoes and has desirable near surface resolution. This requires the thickness of the wear plate be on the order of a wavelength and preferably thinner than ½ wavelength of the acoustic echoes.

It is further an object of the present disclosure to deploy a material for the wear plate that possesses the desirable Young's modulus, high velocity and long wavelength which can resist piercing, albeit being less than a wavelength thick, and to allow direct contact inspection using soft face array probes.

It is further an object of the present disclosure to deploy a material for the wear plate that provides sufficient structural rigidity, albeit being thin, to resist bending and provide intimate contact to and good acoustic coupling to the probe face.

It is further an object of the present disclosure to deploy a material for the wear plate that presents low-sliding friction and has extremely low wear rate when being wrung against test objects that often are hard material such as metal.

It is further an object of the present disclosure to deploy an assembly for the wear plate so that a probe with the wear plate assembly can operate without the need for fluid control.

It is further an object of the present disclosure to deploy a wear plate assembly that can be conveniently put on-and-off the probes.

The following table, "Table-1", provides a summary of all the drawbacks presented by the prior arts that are mitigated or negated by the wear plate assembly according to the present invention. In Table-1, "yes" denotes a drawback presented by the corresponding protective measure. "–" denotes that a drawback is negated by the corresponding protective measure.

TABLE 1

| Drawbacks/ Protective measure | Limited range due to delay-line multiple echoes | Poor near surface resolution | High sliding friction | High repair or replacement cost | Susceptible to piercing damage | Non-replaceable wear member | Requires continuous coupling fluid supply | Not adaptable to soft face probes | Not adaptable to contact inspection w/ soft face array probes |
|---|---|---|---|---|---|---|---|---|---|
| Membrane | — | yes | yes | — | yes | — | — | — | — |
| Plastic cap | — | yes | — | — | — | — | — | — | — |
| Delay line | yes | — | — | — | — | — | — | — | — |
| Stand off device | — | yes | — | — | yes | — | yes | — | — |
| Permanent hard face | — | — | — | yes | — | yes | — | yes | yes |
| Disclosed device | — | — | — | — | — | — | — | — | — |

SUMMARY OF THE INVENTION

The invention disclosed herein avoids or ameliorates the aforementioned drawbacks and problems related to the protective layer or wear plates of ultrasonic probes used in NDT/

DESCRIPTION OF DRAWINGS

FIGS. 3a and 3b are cross-section views of the probe with a circular and four-spot magnetic couplings, respectively.

FIG. 3c shows another embodiment of the probe with a solid cylindrical magnetic coupling.

FIG. 4b is the elevation cross-section view of the embodiment shown in FIG. 4a.

DETAILED DESCRIPTION OF PREFERRED EMBODIMENT OF THE INVENTION

Figure 1A:
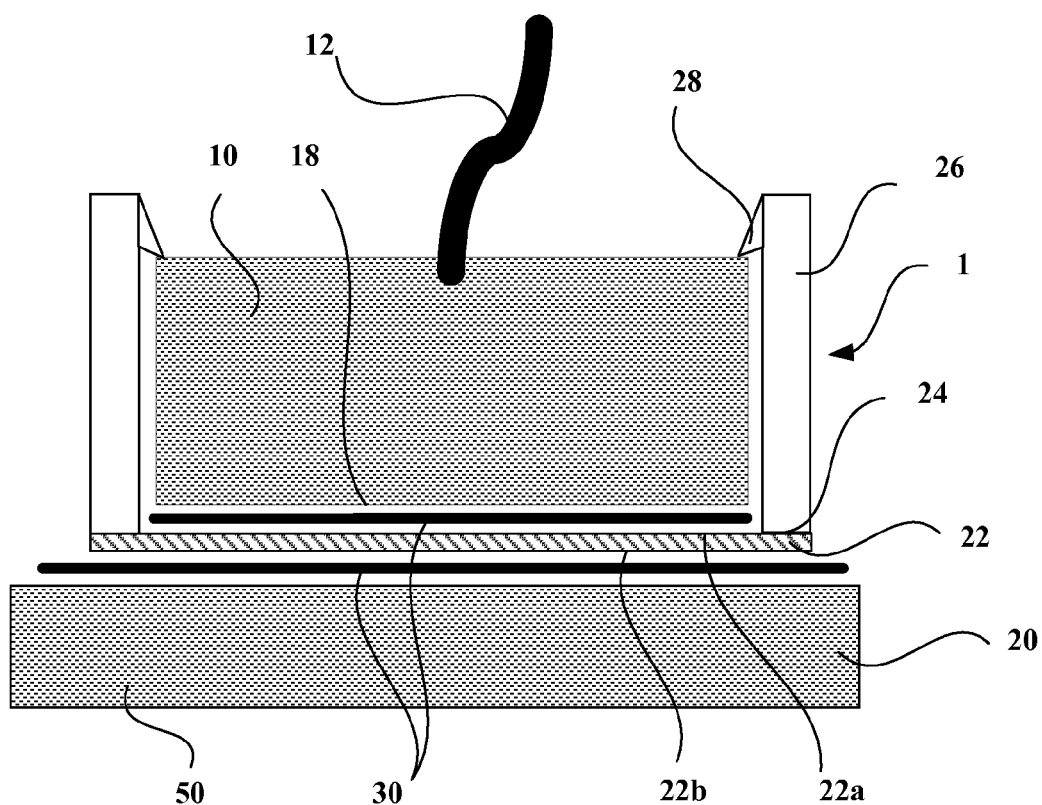
FIG. 1a is a cross-sectional elevation view showing one embodiment of the probe with a removable wear plate assembly according to the present invention.

Referring to FIG. 1a, a preferred embodiment of an ultrasonic probe 1 according to the present invention is shown. This preferred embodiment is chosen to illustrate herein disclosed ultrasonic probe assembly 1 and is not meant to place any restriction on the scope and variations of the invention.

As shown in FIG. 1a, probe assembly 1 comprises an ultrasonic probe 10, a probe cable 12, a removable wear plate 22, a wear plate holder 26 and a layer of liquid couplant 30.

Probe assembly 1, during an inspection operation, is placed on and moved over the surface of a test object 20 to inspect object 20. During the operation, wear plate 22 comes into contact with test object 20 via fluid coupling 30.

Plate holder 26 preferably further comprises a fastening clip 28 to hold probe 10 to be contained within plate holder 26. Wear plate 22, wear plate holder 26 and fastening clip 28 together forms a housing for probe 10, and are configured to protect probe 10 during operation and allow probe 10 to be taken out or put into the housing conveniently. In the embodiment exemplified in FIG. 1a, the fastening clip 28 can be of a flexible clip which is flexible enough to be bent to an open position so that to allow probe 10 to be put into or taken out of the probe assembly 1. Clip 28 also has enough strength to hold transducer 10 in place in its closed position.

It should be recognized that clip 28 can alternatively embody a hinge type of joint, such as a two-positioned hinge joining clip 28 to plate holder 26. This design also allows clip 28 to be either in a closed position to hold probe 10 in place, or an open position to allow probe 10 to be taken out or put into probe assembly 1. In this case, it can be understood that clip 28 does not have to be flexible.

It can be appreciated by the skilled in the art that mechanism of holding transducer 10 in place and allowing probe 10 to be taken out of or put into the probe assembly 1 can be of many variations, all of which should fall within the scope of the present disclosure. A few alternative holding mechanisms are described later in this description.

As can be seen, the above design provides a convenient way of replacing wear plate 22, which can be worn from time to time being wrung against the hard, and most of time not perfectly smooth surface of test object 20.

As can be appreciated by the skilled in the art, the size and strength of clip 28 is configured so that clip 28 is substantially contiguous to the upper surface of probe 10, urging a pressure on probe 10 so that probe 10 presses onto wear plate 22 evenly across wear plate surface via liquid coupling 30. Wear plate holder 26 and clip 28 are also configured to hold probe 10 snuggly so that probe 10 does not separate or decouple from wear plate 22 while probe assembly 1 moves vigorously during inspection operations.

Figure 1B:
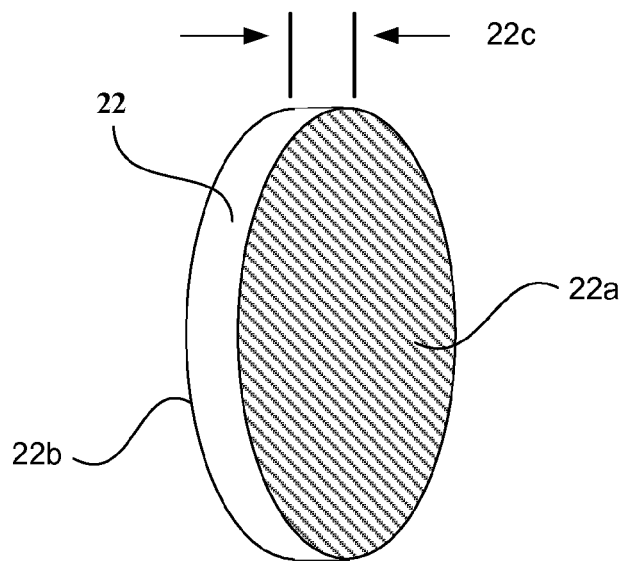
FIG. 1b is a perspective view of the disc of the wear plate possessing characteristics according to the present invention.

As shown in FIG. 1b, another novel aspect of the herein disclosed probe assembly is that the material and fabrication of wear plate 22 possesses many characteristics that are desirable for the inspection operation.

Wear plate materials such as metals, for example titanium, cermets for example titanium carbide (TiC) in nickel-molybdenum matrix or ceramic alloys for example silicon aluminum oxi-nitride (sialon), zirconium toughened alumina (ZTA) or partially stabilized zirconia (PSZ) are preferably chosen for possessing the following characteristics.

It is worth noting that the use of wear plate 22 of one of metals, cermets or ceramic alloys is preferably fabricated to be thinner than a wavelength of the acoustic pulses that are typically used for NDT/NDI inspections, providing a desirable near surface working range of a few wavelengths in the test object material.

Preferred wear plate materials exhibit high compression sound speed (>5500 m/s) permitting a thicker wear plate than slower materials for any a given wavelength or fraction thereof. A larger thickness provides increased protection against bending or piercing damage to the probe, and for a given bending force, reduces maximum tensile stress in the plate, the risk of plate fracture, and bending deflection of the plate.

Preferred wear plate materials also have the desirable hardness (>2 GPa), and -elastic modulus (>100 GPa), to prevent piercing damage and therefore soft-faced probes, such as array probes can be used. The combined high hardness, modulus and thickness of the wear plate limits plate bending and allows soft-faced array probes to be placed in intimate contact with wear plate 22 and therefore maintain a thin acoustic coupling layer 30 therebetween.

Preferred wear plate materials have high tensile strength (>200 MPa), high flexural strength (>500 MPa), and high fracture toughness (>5 $MPa/m^{0.5}$) to resist cracking under pressure from contact with the test object.

Sliding friction between wear plates and test objects remains low because the hard surface of the preferred plate materials do not deform and interlock with test object surface asperities.

The combination of characteristics of wear plate materials as described above provide the possibility of having the wear plate to be fabricated to the desired thinness (0.05-0.5λ) while being structurally sufficient to protect the soft-faced probes.

DETAILED DESCRIPTION OF ALTERNATIVE EMBODIMENTS OF THE INVENTION

The following design variations from the preferred embodiment should be recognized by those skilled in the art to be within the scope of the present disclosure. The description of the following alternative embodiments focuses on the portion of the embodiments that varies from the preferred embodiment, and should be construed to complement the preferred embodiment.

Figure 2:
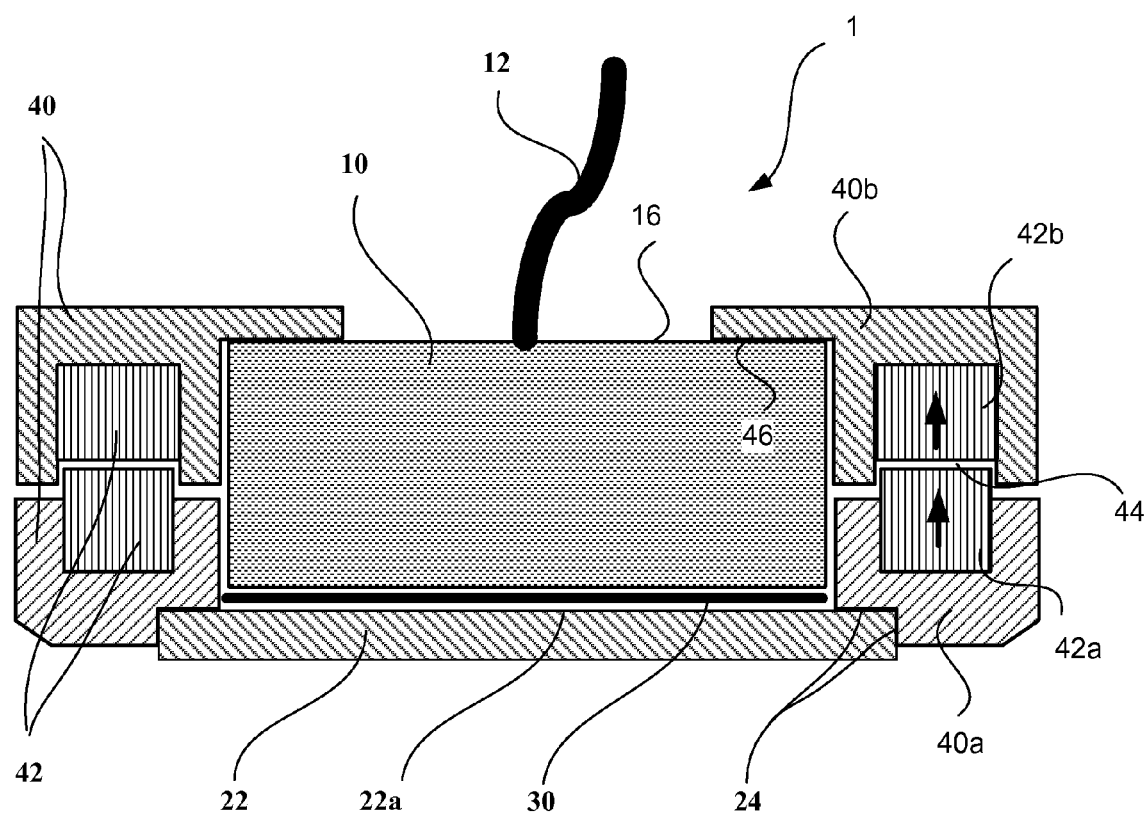
FIG. 2 is an elevation cross-section view showing an alternative embodiment of the probe wherein the upper and lower parting of the probe housing is jointed by a magnetic coupling.

Reference is now turned to FIG. 2, wherein an elevation view of an alternative embodiment is shown. The major variation in this embodiment includes that the plate holder and fastening structure in the preferred embodiment are modified into two parts, lower part 40a and an upper part 40b. Lower part 40a and upper part 40b further include a few pairs of magnetic couplings, such as 42a and 42b, which are correspondingly disposed in 40a and 40b in a symmetric manner. During normal inspection usage, magnetic couplings 42a and 42b keeps the upper and lower plate holder 40 together to hold probe 10 in place. Similar to the preferred embodiment, probe mating surface 46 of upper plate holder 40 is configured to be substantially contiguous to the upper surface of probe 10, urging a pressure on probe 10 so that probe 10 presses onto wear plate 22 evenly across wear plate surface via liquid coupling 30. Wear plate holder 40, when closed by magnetic force of magnetic couplings 42a and 42b, are also configured to hold probe 10 snuggly so that probe 10 does not transition in its position when subjected to vigorous moves during inspection operations.

It can be seen in FIG. 2 that, when it is required to change a wear plate 22 or adjust the liquid coupling, this embodiment allows operator to easily open the probe assembly 1 by breaking the magnetic force and separating the two parts of plate holder, 40a from 40b.

An additional advantage of this embodiment is that the magnetic coupling allows some amount of manufacturing tolerance since a small amount of misalignment can be compensated by the magnetic force.

Different variations of the magnetic couplings are exemplified in FIGS. 3a, 3b and 3c. It should be appreciated that many variations of configuration of magnetic couplings 42 can be employed, and they are all within the scope of the presently disclosed matter.

In FIG. 3a, a whole circle of magnet 42a is embedded in lower plate holder 40a. The same and symmetric configuration is applied to upper plate holder 40b (not shown).

In FIG. 3b, four individual, cylindrical magnets 42a are deposed and evenly distributed in lower plate holder 40a. The same, symmetric and corresponding configuration should be applied to upper plate holder 40b (not shown).

Yet another configuration of magnet 42 is shown in FIG. 3c, in which the whole plate holder 40 is made of magnetic material, and the plate holder 40 becomes the magnetic coupling 42 itself.

It should be noted that magnetic couplings can be formed by two or more permanent magnet couplings aligned north-pole to south-pole or by one or more permanent magnet couplings so aligned and one or more permeable magnetic couplings.

Figure 4A:
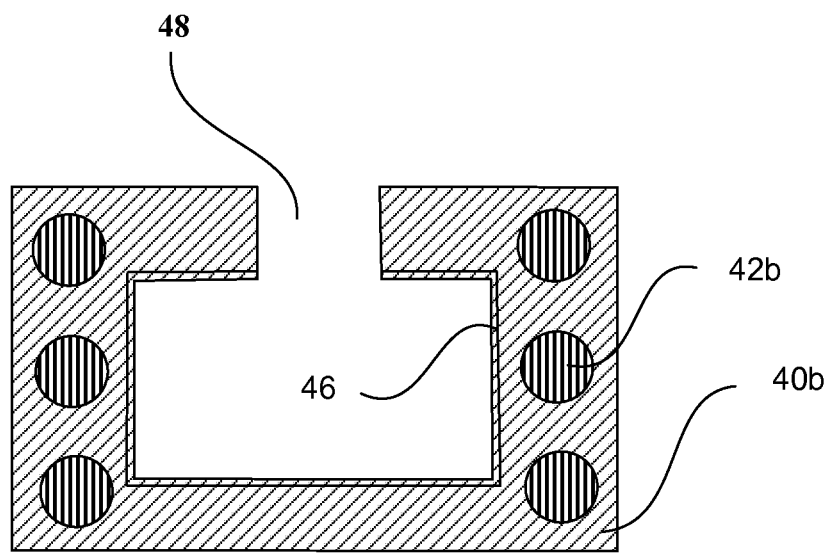
FIG. 4a is a cross-section view of yet another embodiment of the probe wherein the probe housing is of rectangular shape with six individual magnetic couplings.

Referring now to FIG. 4a, yet another alternative embodiment of plate holder 40 is shown to feature a rectangular shaped plate holder 40b (upper part of plate holder 40). This embodiment suits the situation wherein rectangular transducers are employed. It should be noted that any shape of plate holder can be utilized to fit corresponding shapes of probe 10, which falls within the scope of the present disclosure.

In this embodiment, a slot 48 is preferably machined on upper plate holder 40b to allow convenient placement of upper plate holder 40b around probe cable 12.

Figure 4B:
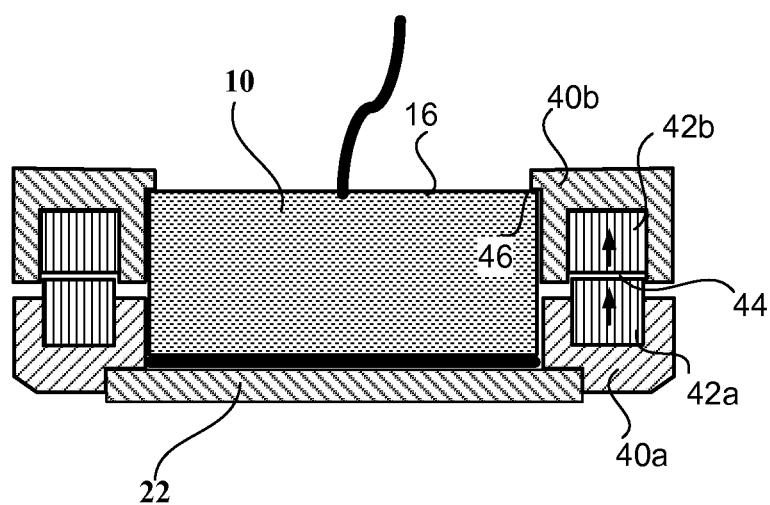

As shown in FIG. 4b, similar to embodiments featuring round plate holders as described above, magnetic couplings 42a and 42b are embedded within plate holder 40a and 40b. It should be understood that variations in magnetic couplings, associated with the alternative embodiments shown in FIGS. 3a, 3b and 3c can also be applied to this embodiment featuring rectangular plate holders and should all be within the scope of the present disclosure.

It should also be noted that variations in combinations of the shapes of plate holders and the arrangement of the magnetic couplings can all be appreciated by those skilled in the art and fall within the scope of presently disclosed invention.

It should also be noted that other variations in fastening coupling, besides magnetic coupling can be employed and easily appreciated by those skilled in the art. One example is to apply pressure fitting snap-and-click coupling to the upper and lower part of plate holder, 40a and 40b respectively. It can be understood that this configuration can also serve the purpose of providing convenient measure to open and close the probe assembly.

What is claimed is:

1. A wear-plate assembly suitable for being configured to form a housing for an ultrasonic probe generating and receiving ultrasonic signals, the wear-plate assembly comprising:
a covering plate that has a thickness less than a wavelength of the ultrasonic signals, wherein the probe is in a testing status when a testing surface of the probe is engaged with the covering plate via a liquid coupling,
a plate holder further comprising a first holder and a second holder, the first holder being attached to the covering plate;
a plate holder joining member connecting the first holder and the second holder and being configured to allow the housing to be at an open or a closed position to allow the probe to be put into or taken out of the housing, respectively,
wherein the wear-plate assembly is configured so that when the probe is placed in the housing, the probe is in the testing status,
wherein the covering plate is made of material that has an ultrasonic sound speed higher than 5500 m/s, an elastic modulus higher than 100 GPa, a hardness higher than 2 GPa, a tensile strength higher than 200 MPa, a flexural strength higher than 500 MPa, and fracture toughness greater than 5 MPa/m$^{0.5}$.

2. The wear-plate assembly of claim 1, in which the second holder is a clip member, and the joining member is a hinge member configured to keep the clip to be in an open or a closed position to allow the probe to be put into or taken out of the housing, respectively.

3. The wear-plate assembly of claim 1, in which the plate holder joining member comprises two or more pairs of magnetic couplings embedded within the first and the second holder, with each corresponding pair of the magnetic couplings being disposed in symmetric and corresponding positions in the first and the second holder.

4. The wear-plate assembly of claim 3, in which each pair of the magnetic couplings have the same size and configuration.

5. The wear-plate assembly of claim 3, in which the magnetic couplings have the shape of cylinders.

6. The wear-plate assembly of claim 1, in which the plate holder joining member comprises one pair of magnetic couplings disposed at the corresponding surfaces of the first and the second holder where the first and the second holder meet.

7. The wear-plate assembly of claim 1, in which the first holder and the second holder have the shape of a cylinder that fits a cylindrical transducer.

* * * * *